United States Patent
Yoo et al.

(10) Patent No.: US 10,371,544 B2
(45) Date of Patent: Aug. 6, 2019

(54) VIBRATING HAPTIC DEVICE FOR THE BLIND

(71) Applicants: Kevin Yoo, East Haven, CT (US); Keith Kirkland, Newark, NJ (US); Yangyang Wang, New Rochelle, NY (US)

(72) Inventors: Kevin Yoo, East Haven, CT (US); Keith Kirkland, Newark, NJ (US); Yangyang Wang, New Rochelle, NY (US)

(73) Assignee: WEARWORKS, Brooklyn, NY (US)

( * ) Notice: Subject to any disclaimer, the term of this patent is extended or adjusted under 35 U.S.C. 154(b) by 0 days.

(21) Appl. No.: 15/807,494

(22) Filed: Nov. 8, 2017

(65) Prior Publication Data

US 2018/0321056 A1 Nov. 8, 2018

Related U.S. Application Data

(60) Provisional application No. 62/501,140, filed on May 4, 2017.

(51) Int. Cl.

| | |
|---|---|
| *A61F 9/08* | (2006.01) |
| *A61H 3/06* | (2006.01) |
| *G06F 3/01* | (2006.01) |
| *G01C 21/36* | (2006.01) |
| *G09B 21/00* | (2006.01) |

(52) U.S. Cl.
CPC ......... *G01C 21/3652* (2013.01); *A61H 3/061* (2013.01); *G06F 3/014* (2013.01); *G09B 21/003* (2013.01); *A61F 9/08* (2013.01); *A61H 2003/063* (2013.01); *A61H 2201/165* (2013.01)

(58) Field of Classification Search
CPC .............................. G06F 1/163; A61B 5/0492
See application file for complete search history.

(56) References Cited

U.S. PATENT DOCUMENTS

| | | | |
|---|---|---|---|
| 8,378,979 | B2 | 2/2013 | Frid et al. |
| 8,441,437 | B2 | 5/2013 | Rank |
| 8,493,344 | B2 | 7/2013 | Fleizach et al. |
| 8,576,171 | B2 | 11/2013 | Grant |
| 8,576,174 | B2 | 11/2013 | Cruz-Hernandez et al. |
| 8,681,106 | B2 | 3/2014 | Fleizach et al. |
| 8,751,971 | B2 | 6/2014 | Fleizach |
| 9,009,612 | B2 | 4/2015 | Fleizach et al. |
| 9,082,239 | B2 | 7/2015 | Ricci |
| 9,083,821 | B2 | 7/2015 | Hughes |
| 9,092,954 | B2 | 7/2015 | Visitacion et al. |
| 9,123,186 | B2 | 9/2015 | Ricci |

(Continued)

FOREIGN PATENT DOCUMENTS

| | | |
|---|---|---|
| WO | 2015083183 A4 | 6/2015 |
| WO | 2017014542 A1 | 1/2017 |

*Primary Examiner* — Fabricio R Murillo Garcia
(74) *Attorney, Agent, or Firm* — Gearhart Law, LLC

(57) ABSTRACT

A device and system for aiding in navigation. The system includes a vibrating haptic device, including a printed circuit board configured to determine a geographic position of a user, a battery, one or more isolation pads, and a plurality of actuators, and a mobile electronic device coupled to the vibrating haptic device, wherein the mobile electronic device is configured to analyze data gathered by the vibrating haptic device and determine a geographic position and angle of a user.

16 Claims, 17 Drawing Sheets

(56) References Cited

U.S. PATENT DOCUMENTS

| | | | |
|---|---|---|---|
| 9,274,603 B2 | 3/2016 | Modarres et al. | |
| 9,383,820 B2 | 7/2016 | Fleizach et al. | |
| 9,466,187 B2 | 10/2016 | Grant et al. | |
| 9,553,625 B2 | 1/2017 | Hatanaka et al. | |
| 9,594,444 B2 | 3/2017 | Bae et al. | |
| 2011/0148607 A1* | 6/2011 | Zeleny | A41D 13/0015 340/407.1 |
| 2014/0310594 A1 | 10/2014 | Ricci et al. | |
| 2015/0025355 A1* | 1/2015 | Bailey | A61B 5/681 600/390 |
| 2015/0220109 A1* | 8/2015 | von Badinski | G01P 15/00 340/539.12 |
| 2015/0290454 A1 | 10/2015 | Tyler et al. | |
| 2016/0109949 A1 | 4/2016 | Park | |
| 2016/0165965 A1 | 6/2016 | Ellis et al. | |
| 2016/0267344 A1* | 9/2016 | Yamamoto | G06K 9/3241 |
| 2017/0075701 A1 | 3/2017 | Ricci et al. | |

* cited by examiner

VIBRATING HAPTIC DEVICE FOR THE BLIND

CLAIM OF PRIORITY

This application claims priority to U.S. Provisional Patent Application No. 62/501,140, filed May 4, 2017 and referenced herein in its entirety.

FIELD OF THE EMBODIMENTS

This invention relates to directional aids and, in particular, to wearable haptic navigation devices for the Blind and Visually Impaired (BVI).

BACKGROUND OF THE EMBODIMENTS

In order to navigate, individuals who are visually impaired must use means other than the use of their eyes. For many, a cane is an indispensable first step towards navigation independence. However, the use of canes and other methods, like step counting, can result in inaccurate estimations of user's current location. This is due to the estimation involved with such methods.

A method of easily tracking a location of a user and providing non-visual cues to the user, to aid the user in navigating between two or more locations, is needed.

Examples of Related Art are Described Below:

U.S. Pat. No. 8,378,979 generally describes haptic feedback being provided to a user of an electronic device, such as an electronic book reader device, to confirm receipt of user input or otherwise convey information to the user. The haptic feedback may be provided more quickly than a display update time of a display of the electronic device. Different patterns, durations, and/or intensities of haptic feedback may be used in response to different events.

U.S. Pat. No. 8,441,437 generally describes triggering haptic sensations based on sound output from a computer device. A portion of sound data is stored that is output to a user as audio from an application program running on a computer. The portion of sound data is analyzed using intelligent heuristics to extract at least one sound feature from the sound data. The execution of at least one haptic effect is triggered based on the sound feature, where the haptic effect is commanded to the haptic feedback device approximately correlated to the output of the portion of sound to the user as audio. The haptic effect causes a haptic sensation to be output to the user. Different haptic effects can be associated with different sound features, frequency ranges, amplitudes, etc.

U.S. Pat. No. 8,493,344 generally describes an accessibility method that is performed by an electronic device with a display and a touch-sensitive surface. The method includes: displaying a plurality of user interface elements on the display; in response to detecting a first user interface navigation gesture by a finger on the touch-sensitive surface, navigating in the plurality of user interface elements in accordance with a current navigable unit type; in response to detecting a first user interface navigation setting gesture on the touch-sensitive surface: changing the current navigable unit type from the first navigable unit type to a second navigable unit type; and outputting accessibility information about the second navigable unit type; after changing the current navigable unit type, in response to detecting a second user interface navigation gesture by the finger on the touch-sensitive surface, navigating in the plurality of user interface elements in accordance with the current navigable unit type.

U.S. Pat. No. 8,576,171 generally describes systems and methods for providing haptic feedback to touch-sensitive input devices. For example, one disclosed system includes an input device having a housing having an exterior surface; a touch-sensitive surface configured to transmit a contact signal indicating a contact with the touch-sensitive surface; a sensor disposed within the housing, the sensor configured to sense movement of the input device and to transmit a sensor signal indicating movement of the input device; an actuator disposed within the housing, the actuator configured to output a haptic effect based on an actuator signal, the actuator signal based at least in part on the contact signal.

U.S. Pat. No. 8,576,174 generally describes an electronic device and method of operating comprises a housing; a base coupled to the housing; and an electro-mechanical transducer coupled to the base, the electro-mechanical transducer configured to operate in a resonant mode and output a haptic effect upon receiving a drive signal at a predetermined drive frequency. In an embodiment, the electro-mechanical transducer further comprises a plurality of electro-mechanical transducers, each electro-mechanical transducer configured to operate in its respective resonant mode and output a respective haptic effect upon receiving a drive signal having a predetermined drive frequency. Alternatively or additionally, the electro-mechanical transducer further comprises a plurality of spaced apart electro-mechanical devices coupled thereto in a serial fashion between a first end proximal to the base and a second end distal to the base.

U.S. Pat. No. 8,681,106 generally describes an accessibility method that is performed by an electronic device with a display and a touch-sensitive surface. The method includes: mapping at least a first portion of the display to the touch-sensitive surface; concurrently displaying a plurality of user interface containers on the display; detecting a user interface container selection event that selects a first user interface container in the plurality of user interface containers; and, in response to detecting the user interface container selection event: ceasing to map the first portion of the display to the touch-sensitive surface, and proportionally mapping the first user interface container to be substantially coextensive with the touch-sensitive surface.

U.S. Pat. No. 8,751,971 generally describes an electronic device that presents a first user interface element of a first type and a second user interface element of a second type. In a sighted mode, the device detects a first interaction with the first user interface element, and performs an operation in accordance with sighted-mode gesture responses for the first user interface element. The device detects a second interaction with the second user interface element, and performs an operation in accordance with sighted-mode gesture responses for the second user interface element. In an accessible mode, the device detects a third interaction with the first user interface element, and performs an operation in accordance with accessible-mode gesture responses for the first user interface element. The device detects a series of interactions with the second user interface element; and, for each interaction, performs an operation in accordance with the sighted-mode gesture responses for the second user interface element.

U.S. Pat. No. 9,009,612 generally describes a method that is performed by an accessible electronic device with a display and a touch-sensitive surface. The method includes: displaying a plurality of user interface elements on the display, wherein a current focus is on a first user interface element; detecting a first finger gesture on the touch-sensitive surface, wherein the first finger gesture is independent of contacting a location on the touch-sensitive surface that corresponds to a second user interface element; and, in response to detecting the first finger gesture: changing the current focus from the first user interface element in the plurality of user interface elements to the second user interface element in the plurality of user interface elements; and outputting accessibility information associated with the second user interface element.

U.S. Pat. No. 9,082,239 generally describes methods, systems, and a computer readable medium for maintaining a persona of a vehicle occupant and, based on the persona of the vehicle occupant and vehicle-related information, performing an action assisting the vehicle occupant.

U.S. Pat. No. 9,083,821 generally describes a method that is performed by one or more processes executing on a computer systems includes receiving an audio signal comprising a range of audio frequencies including high frequencies and low frequencies, converting a first portion of the range of audio frequencies into haptic data, shifting a second portion of the range of audio frequencies to a different range of audio frequencies, and presenting at least one of the converted first portion and the shifted second portion to a human user. Other implementations of this aspect include corresponding systems, apparatus, and computer program products.

U.S. Pat. No. 9,092,954 generally describes a wearable device that may be configured to generate feedback based on an event that occurs in an environment related to the wearable device. The wearable device may include, for example, a processor configured to generate a control signal representative of an event occurring in an environment related to the wearable device and at least a first haptic output device disposed at a first position at the wearable device. The first haptic output device may be configured to provide haptic feedback based on the generated control signal.

U.S. Pat. No. 9,123,186 generally describes methods and systems for a vehicle control system to control user access to vehicle tasks, functions and/or operations based on rights and privileges set forth in user accounts.

U.S. Pat. No. 9,274,603 generally describes systems and methods of providing haptic feedback based on media content and one or more external parameters used to customize the haptic feedback. The system may modify or otherwise alter haptic feedback that is determined using the media content alone. In other words, the system may use both the media content and the external parameters to determine haptic feedback that should be output to the user or others. The external parameters may include, for example, sensor information, customization information, and/or other external parameters that may be used to customize the haptic feedback.

U.S. Pat. No. 9,383,820 generally describes technology, which can be implemented as a method, apparatus, and/or computer software embodied in a computer-readable medium, and which, among other things, be used to create custom vibration patterns in response to user input, for example, in response to the user tapping out a desired pattern on the display of a mobile device. For example, one or more aspects of the subject matter described in this disclosure can be embodied in one or more methods that include receiving tactile input from a user of an electronic device specifying a custom vibration pattern, in concert with receiving tactile input, providing visual feedback to the user corresponding to the received tactile input, and storing the specified custom vibration pattern for use by the electronic device to actuate haptic feedback signaling a predetermined notification event.

U.S. Pat. No. 9,466,187 generally describes a system for managing a plurality of wearable devices on a user that receives information to be conveyed using haptic effects and determines an intent of the information. The system then determines, for each of the plurality of wearable haptic devices, a location of the wearable haptic device on the user and a haptic capability. The system then maps the information as a haptic effect to one or more of the wearable haptic devices based at least on the determined locations on the user and the haptic capabilities.

U.S. Pat. No. 9,553,625 generally describes a wearable device that is coupled to a band including multiple modular functional band links that are each electrically and mechanically connected to one or more other of the band links and/or the wearable device and include one or more electronic components. In various implementations, the wearable device may receive identifiers from each of the band links, determine functionality available using the identifiers, and communicate with the band links to utilize the determine functionality. In some implementations, the band links may include multiple different output devices and the wearable device may determine to provide an output pattern and signal the respective output devices according to the output pattern. In various implementations, the band links may include multiple different input devices and the wearable device may receive input indications from the input devices and perform an action based on a pattern in which the input indications were detected by the respective input devices.

U.S. Pat. No. 9,594,444 generally describes a haptic feedback method that includes providing a user with an image that is updated based on a collision event, generating collision data including a type of the collision event and an impulse amount, generating a haptic pattern based on the collision data, and generating a vibration based on the haptic pattern.

U.S. Patent Publication No. 2014/0310594 generally describes methods and systems for a driver or impairment assistive on board vehicle display, inactive control surface, and customization of a vehicle interface based on one or more of user impairment, user medical condition, user age, user physical condition, user driving characteristic and driving history.

U.S. Patent Publication No. 2015/0290454 generally describes systems and methods for management of brain and body functions and sensory perception. For example, the present invention provides systems and methods of sensory substitution and sensory enhancement (augmentation) as well as motor control enhancement. The present invention also provides systems and methods of treating diseases and conditions, as well as providing enhanced physical and mental health and performance through sensory substitution, sensory enhancement, and related effects.

U.S. Patent Publication No. 2016/0165965 generally describes interactive apparel to teach and aid proper use without undue situational and apparel knowledge, without undue physical demands, and without undue secondary action.

U.S. Patent Publication No. 2017/0075701 generally describes methods and systems for a driver or impairment assistive on board vehicle display, inactive control surface, and customization of a vehicle interface based on one or more of user impairment, user medical condition, user age, user physical condition, user driving characteristic and driving history.

U.S. Patent Publication No. 2016/0109949 generally describes a haptic feedback apparatus using a vibration atmosphere compensation algorithm may include: a vibration sensor configured to collect vibration atmosphere data; a memory configured to store a pattern for compensating for the vibration atmosphere and a haptic pattern corresponding to a touch input; a controller configured to generate a pattern for compensating for the vibration atmosphere based on the vibration atmosphere data, synthesize the haptic pattern stored in the memory with a pattern for compensating for the vibration atmosphere, when a touch input of the user is detected through a touch panel, and output the synthesized haptic pattern; and an actuator configured to vibrate according to the haptic pattern outputted from the controller.

International Patent Publication No. WO2015083183 generally describes a hand wearable haptic feedback based navigation device for distance sensing which has the flexibility of attachment and detachment of the navigation sensors and has the flexibility of sensing the distance of the obstacle in multiple directions covering maximum 180 degrees in the direction of pointing of the hand. The device measures the distance of obstacle using sensors at the tip of a finger. The measurement is broken down into categories on the basis of distance. This category is eventually informed to the user via haptic feedback actuators strategically located on the specific finger. The feedback is taken to three dimensions by mapping the hand's spatial orientations using Inertial measurement units.

International Patent Publication No. WO2017014542 generally describes a wearable haptic pattern display device for visually impaired people and, more specifically, to a wearable haptic pattern display device for visually impaired people, the device: being formed in a compact size such that a user can easily carry the device, and having, on a front surface of a display device body, a touch screen in which a touch panel and an electric sensitive panel are integrally coupled, thereby providing a text screen having a combination of various haptic tactile sensations through the touch screen; having, on a rear surface of the display device body, a ring-shaped wearable member for enabling a user to wear the wearable member on a finger, such that the user can simply read the text screen of a haptic tactile sensation displayed on the touch screen by using the thumb while wearing the ring-shaped wearable member on the user's index finger, thereby enabling texts such as news, books, or messages to be read by using the display device regardless of time and place because of a convenience of use and excellent portability thereof; and additionally, having an NFC module on the display device body so as to receive guidance information from NFC tags provided in various places such as the surroundings of roads, the surroundings of intersections or the inside of shops, or on conventional braille signs, such that visually impaired people can easily use the display device.

None of the art described above addresses all of the issues that the present invention does.

SUMMARY OF THE EMBODIMENTS

According to an aspect of the present invention, a device for aiding in navigation is provided. The device includes a printed circuit board configured to determine a geographic position of a user, a battery, one or more isolation pads, and a plurality of actuators.

According to another aspect of the present invention, a system for aiding in navigation is provided. The system includes a vibrating haptic device, including a printed circuit board configured to determine a geographic position of a user, a battery, one or more isolation pads, and a plurality of actuators. The system further includes a mobile electronic device coupled to the vibrating haptic device, wherein the mobile electronic device is configured to analyze data gathered by the vibrating haptic device and determine a geographic position and angle of a user.

It is an object of the present invention to provide the device for aiding in navigation, wherein the device further includes an enclosure configured to house the printed circuit board, the battery, the one or more isolation pads, and the plurality of actuators.

It is an object of the present invention to provide the device for aiding in navigation, wherein the printed circuit board is a flexible printed circuit board.

It is an object of the present invention to provide the device for aiding in navigation, wherein the device further includes a strap for coupling the device to the user.

It is an object of the present invention to provide the device for aiding in navigation, wherein the battery is a rechargeable battery.

It is an object of the present invention to provide the device for aiding in navigation, wherein the isolation pads are configured to mechanically separate the actuators.

It is an object of the present invention to provide the system for aiding in navigation, wherein the system further includes an enclosure configured to house the printed circuit board, the battery, the one or more isolation pads, and the plurality of actuators.

It is an object of the present invention to provide the system for aiding in navigation, wherein the printed circuit board is a flexible printed circuit board.

It is an object of the present invention to provide the system for aiding in navigation, wherein the system further includes a strap for coupling the vibrating haptic device to the user.

It is an object of the present invention to provide the system for aiding in navigation, wherein the battery is a rechargeable battery.

It is an object of the present invention to provide the system for aiding in navigation, wherein the isolation pads are configured to mechanically separate the actuators.

It is an object of the present invention to provide the system for aiding in navigation, wherein the plurality of actuators are selected from the group consisting of piezoelectric actuators, eccentric rotating mass actuators, linear resonant actuators, and bone conduction speakers.

DESCRIPTION OF THE PREFERRED EMBODIMENTS

Figure 1:
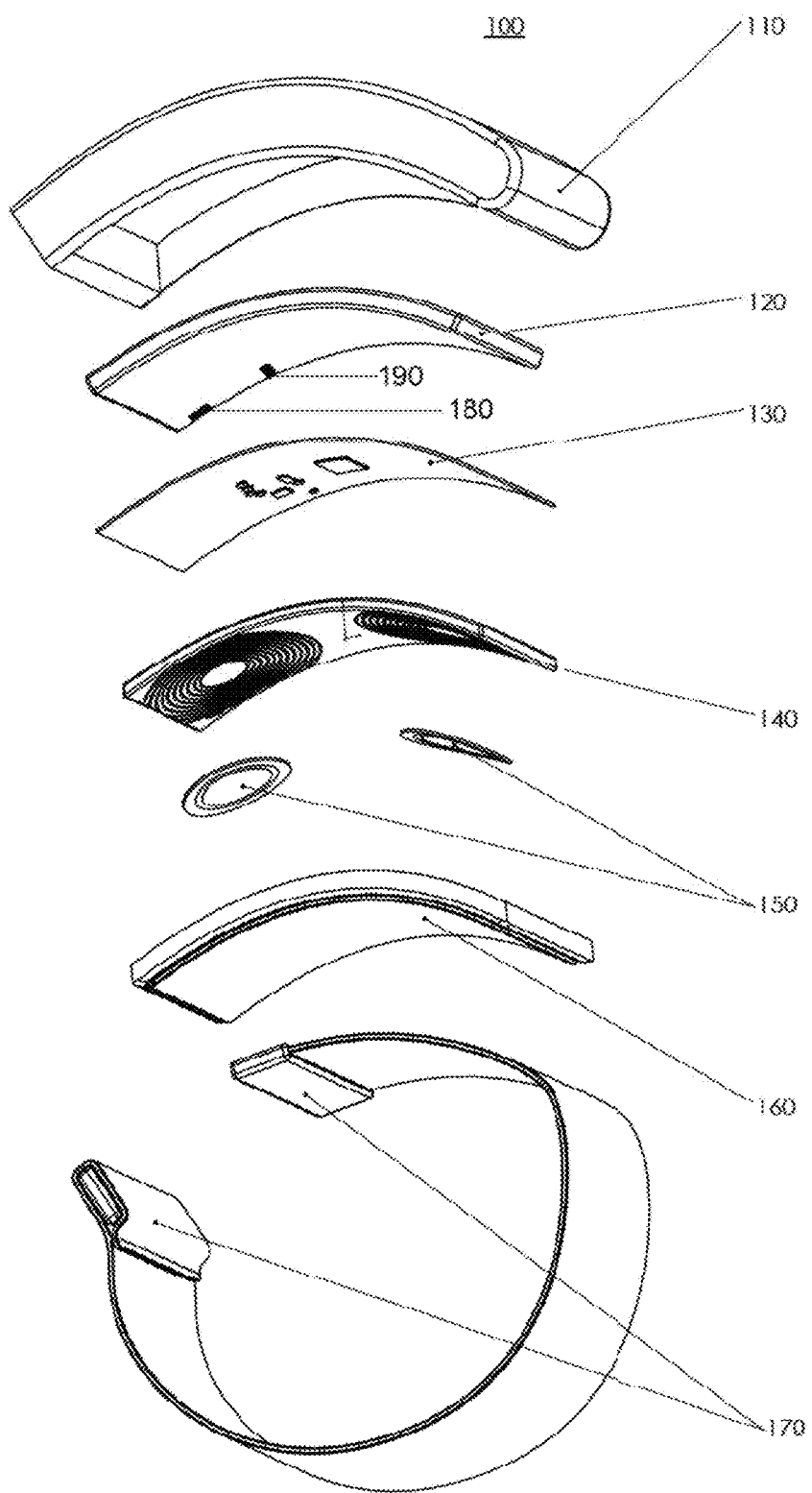
FIG. 1 shows an exploded view of a vibrating haptic device, according to an embodiment of the present invention.
Figure 2:
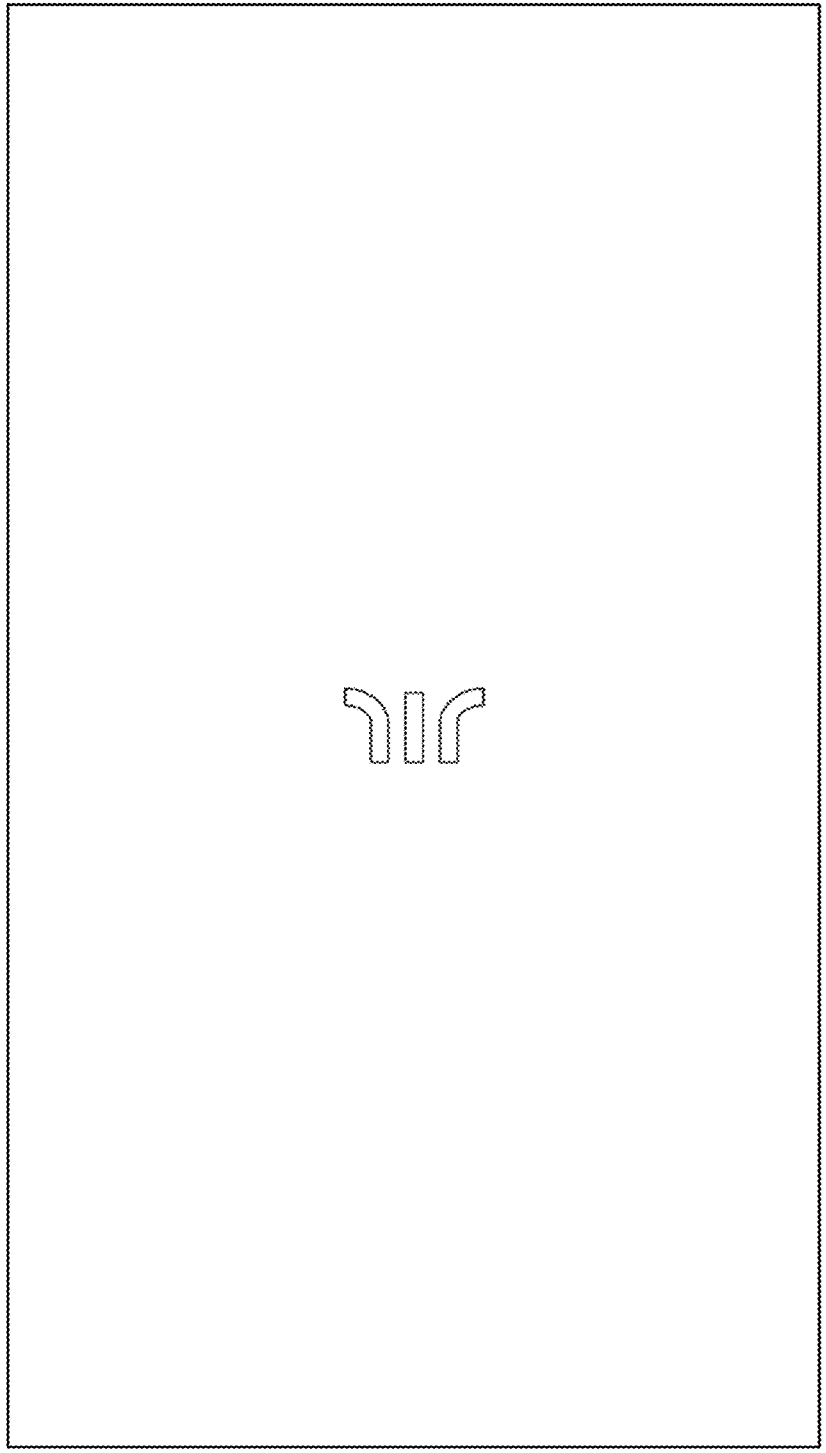
FIG. 2 shows a screenshot of an introduction screen of an application, for use with the present invention, on a mobile electronic device, according to an embodiment of the present invention.
Figure 3:
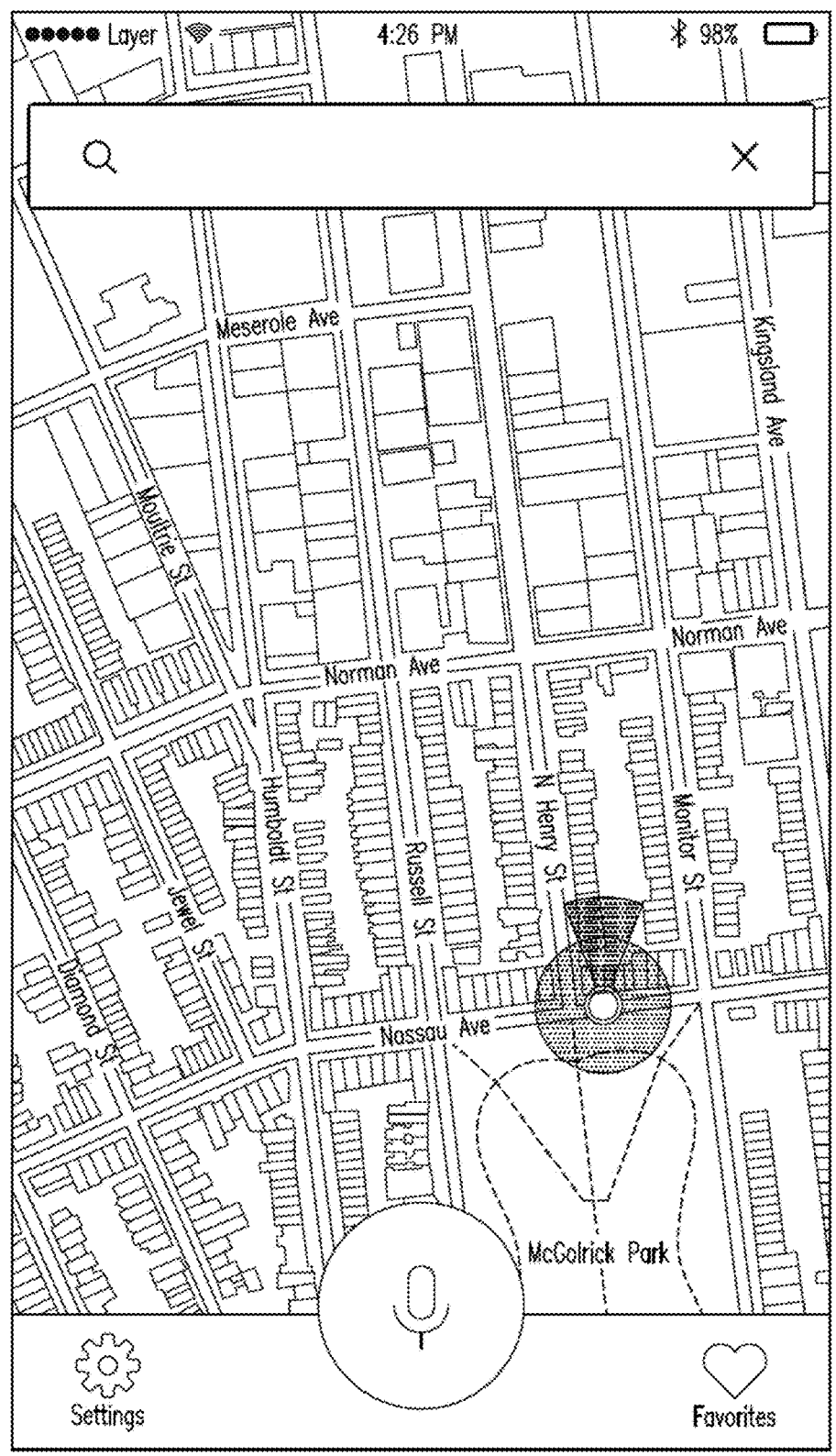
FIG. 3 shows a screenshot of a screen of navigation input options on an application, for use with the present invention, on a mobile electronic device, according to an embodiment of the present invention.
Figure 4:
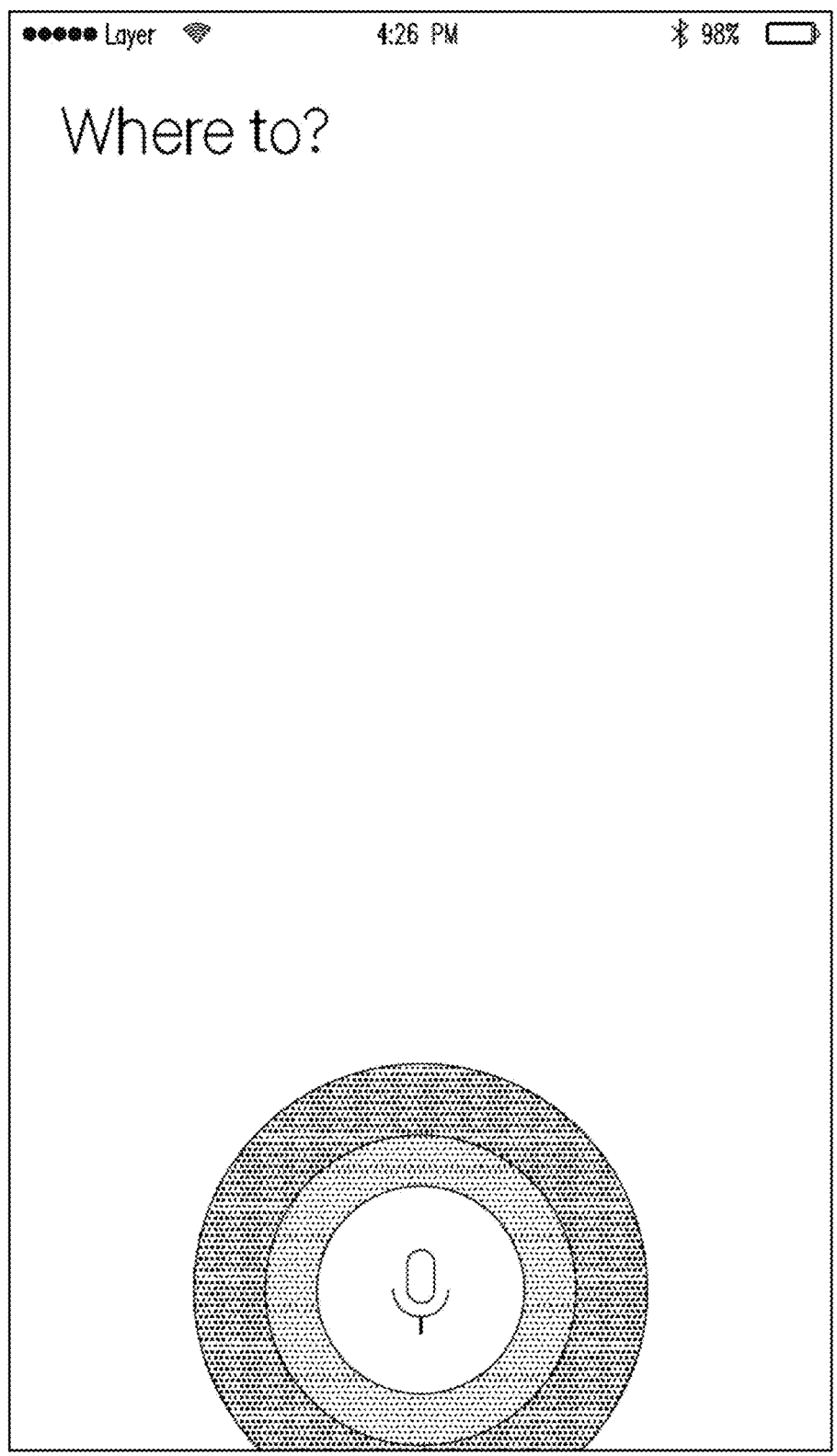
FIG. 4 shows a screenshot of a voice input screen of an application, for use with the present invention, on a mobile electronic device, according to an embodiment of the present invention.
Figure 5:
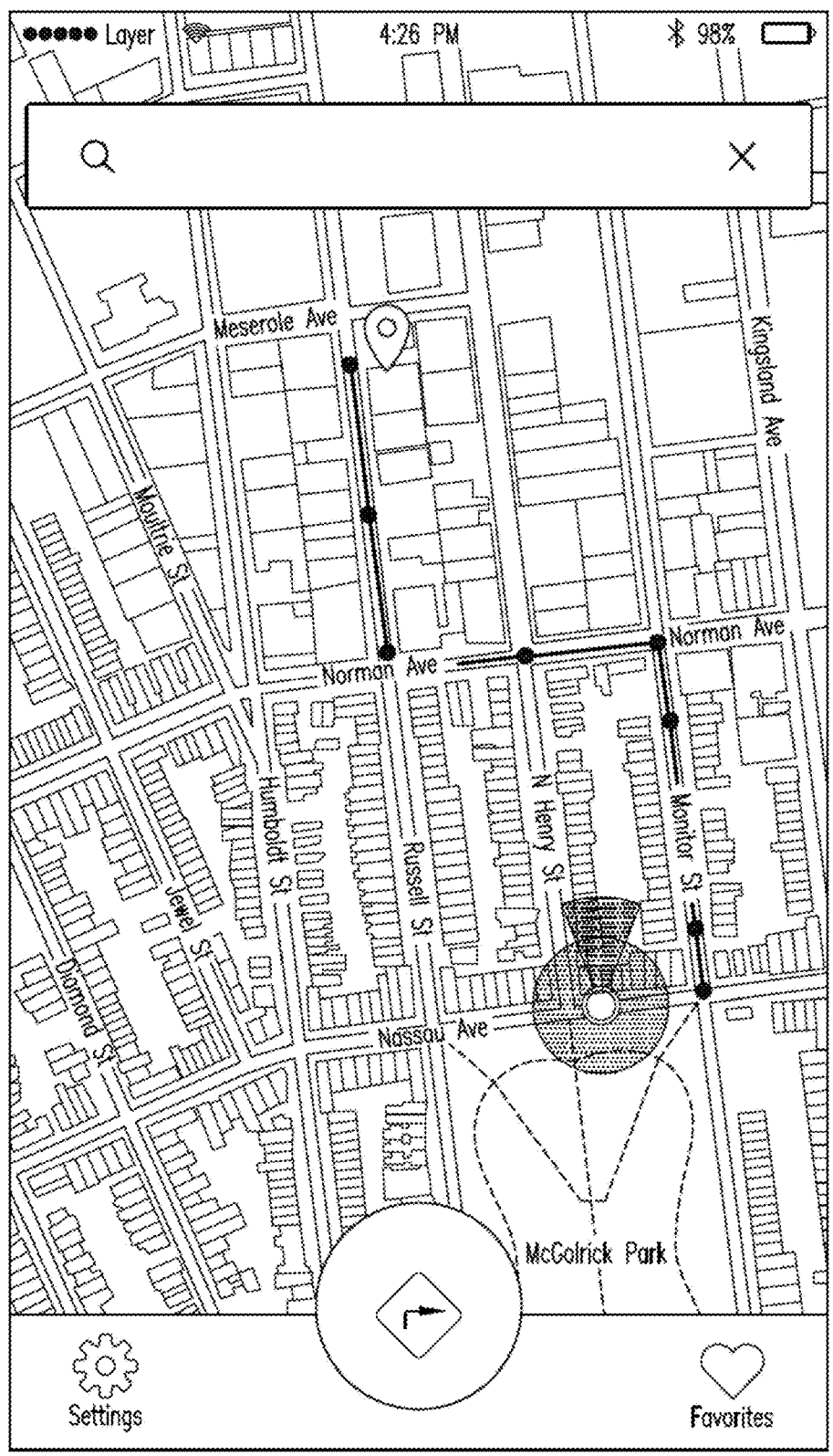
FIG. 5 shows a screenshot of a start screen of an application to begin navigation, for use with the present invention, on a mobile electronic device, according to an embodiment of the present invention.
Figure 6:
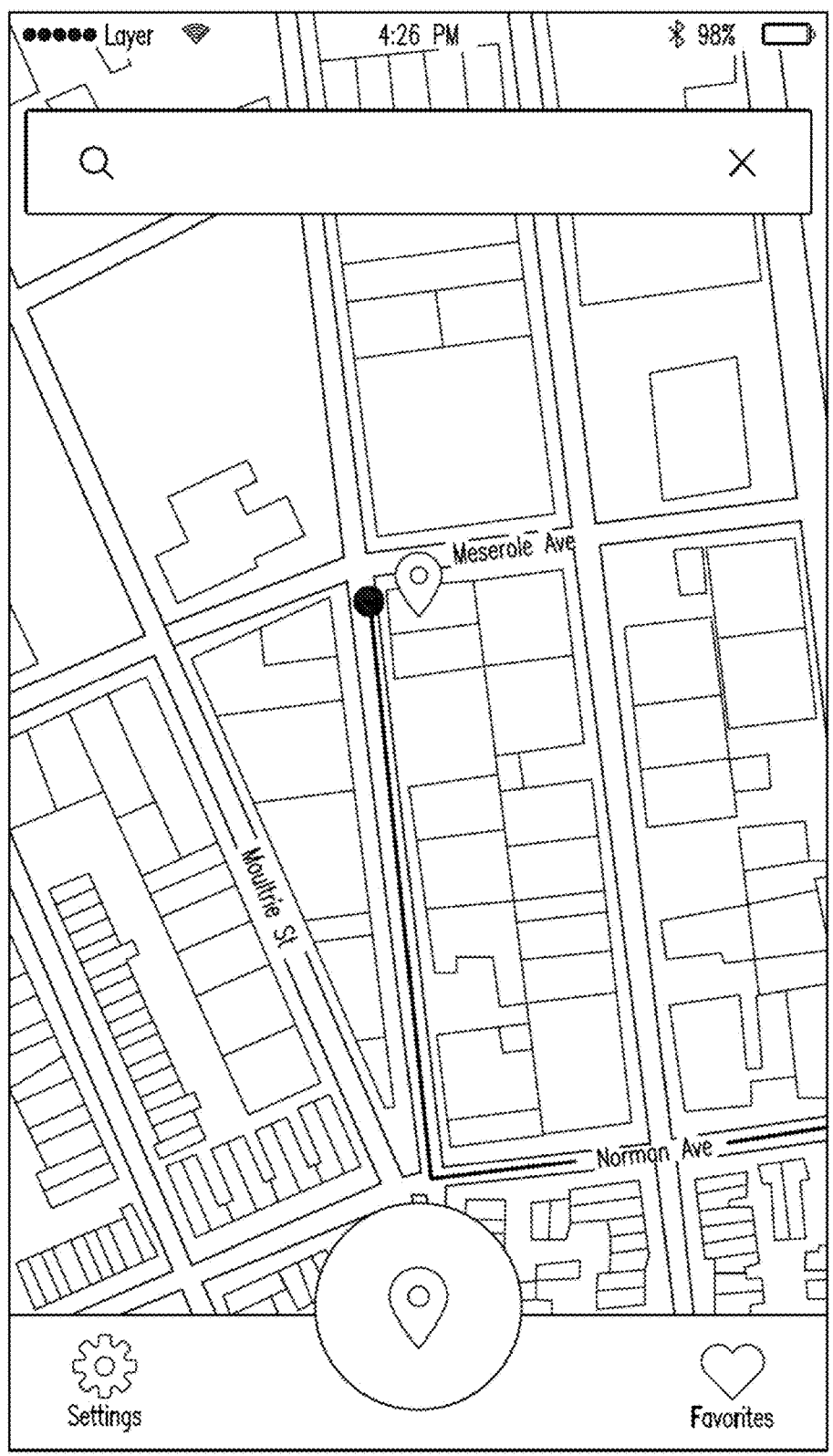
FIG. 6 shows a screenshot of a navigation map on an application, for use with the present invention, on a mobile electronic device, according to an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring now to FIG. 1, an exploded view of a vibrating haptic device 100 is illustratively depicted, in accordance with an embodiment of the present invention.

According to an embodiment, the vibrating haptic device includes an upper enclosure 110 and a lower enclosure 160, the upper 110 and lower 160 enclosures housing a battery 120, a flexible Printed Circuit Board (PCB) 130, one or more isolation pads 140, and a plurality of actuators 150. According to an embodiment, the vibrating haptic device may further include a strap 170, a microphone 180 and/or one or more input channels 190 for inputting one or more electronic devices. According to an embodiment, the haptic device 100 may be configured to be placed on the head, chest, arm, leg, and/or any other suitable location of the user. According to an embodiment, the inputs for the control systems for the vibrating haptic device 100 may include an angular degree of correct/incorrect, a haptic volume, a frequency (e.g., a blink rate as a function of "time_on" and "time_off"), an orientation, a haptic expression (e.g., discreet messages to communicate specific information), haptic experiences (e.g., intuitive experiences such as a "Haptic Corridor"), and/or any other suitable inputs.

According to an embodiment, the PCB further includes one or more ultrasonic sensors configured to use sound waves to measure the distance between the vibrating haptic device 100 and one or more objects.

According to an embodiment, the top enclosure 110 and lower enclosure 160 form a water-resistant seal. According to an embodiment, the enclosure 110, 160 is molded into a single, water-resistant structure. According to an embodiment, the enclosure 110, 160 may further include one or more structures 190 for aiding in vibration dampening and/or isolation of haptic sensations. These structures 190 may, when individual motors actuate, enable the user to tell not only by difference in strength, but by difference in location.

According to an embodiment, the enclosure 110, 160 is configured to ergonomically fit the body part it is being worn on. According to an embodiment, the enclosure 110, 160 is removably coupled to the strap 170. The vibrating haptic device 100 may be configured to be coupled to a wrist, ankle, and/or other suitable location on the user's body. The vibrating haptic device 100 may also be configured to be coupled to one or more objects in the user's possession, such as, e.g., a hat, cane, etc.

According to an embodiment, the battery 120 is rechargeable. According to an embodiment, the battery 120 is removable from the enclosure 110, 160. According to an embodiment, the battery 120 is permanently housed within the enclosure 110, 160. According to an embodiment, the battery 120 is solar powered.

According to an embodiment, the isolation structures 140 (e.g., isolation pads) mechanically separate the actuators 150 and create separation of vibration patterns. The actuators 150 may be piezoelectric actuators, Eccentric Rotating Mass (ERM) actuators, Linear Resonant Actuators (LRAs), bone conduction speakers, and/or any other suitable actuator or actuators.

According to an embodiment, the strap 170 has a clasping mechanism, the clasping mechanism being magnetic on two sides. It is noted, however, that other forms of clasping mechanisms may also be used, while maintaining the spirit of the present invention.

Figure 8:
FIG. 8 shows a front view of an electronic device configured for use in conjunction with the vibrating haptic device, according to an embodiment of the present invention.

According to an embodiment, the vibrating haptic device 100 is part of a system for aiding navigation for the visually impaired. It is noted, however, that the system may also be used by individuals who are not visually impaired. The system may also include one or more mobile electronic devices 1200 (shown in FIG. 8FIG. 8). The one or more mobile electronic devices 1200 may include a smart phone, a tablet, smart watches, and/or any other suitable mobile electronic devices 1200. It is noted, however, that, according to some embodiments, the haptic device 100 may be used as a standalone device without the use of one or more electronic devices 1200. The device 100 may be embedded with GPS technology and/or maps may be stored on the device 100.

According to an embodiment, the vibrating haptic device 100 connects to a custom application that has a unique algorithm for non-visual, non-audial navigation. The algorithm conforms to a method of wayfinding, so the vibrating haptic device's 100 haptic feedback signals/patterns will change depending on if the user is driving, running, biking, walking, or any other means of travel. Determining factors may include, but are not limited to, geolocation (city vs. nature) and speed (current velocity, acceleration).

According to an embodiment, the algorithm may process data such that the vibrating haptic device 100 will provide tactile feedback whenever the user begins navigation, is going the correct way, is going the incorrect way, has a left turn approaching, has a right turn approaching, is close to an intersection, has Points of Interest (POIs) nearby, is approaching roadside, is approaching curbside, etc. According to an embodiment, the algorithm also uses this data to filter out unwanted information, which makes navigation and wayfinding much more accurate.

According to an application, the application uses GPS and/or other wireless signals to locate a position and orientation of the user, and omits any errant data (like signal bounces or magnetic influence within the city, etc.). The application is also a means to offload heavy computing onto mobile electronic device 1200, which decreases hardware cost and/or the size of the device itself, leaving space for high definition haptic components (such as, for example, piezoelectric actuators and their respective drivers) which are not found in the mobile electronic device 1200. The application, being on a phone 1200, also solves a very difficult problem, which is to determine the device's 100 position relative to the user (what is now referred to as omni-directionality, which is usually resolved by complex "dead-reckoning" algorithms). For example, the vibrating haptic device's 100 position relative to the user should not affect what kind of haptic signals are being expressed, since what matters is the user's position relative to his/her navigation route (i.e. arm-swinging should not affect haptics).

According to an embodiment, the vibrating haptic device 100 may be shock-resistant, partially and/or fully-voice activated, screenless, and/or buttonless. According to an embodiment, the vibrating haptic device 100 may include one or more layers of haptic expressiveness. According to an embodiment, the haptic device 100 may be used in conjunction with, or may incorporate, other forms of sensory output such as, but not limited to, audio output (using headphones and/or any other suitable device).

Figure 9:
FIG. 9 shows a perspective view of a vibrating haptic device, according to an embodiment of the present invention.
Figure 10:
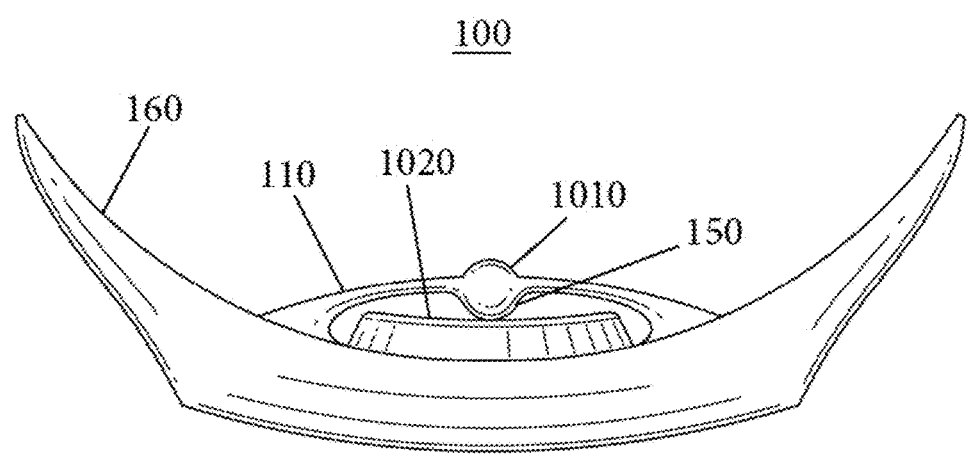
FIG. 10 shows a side view of a vibrating haptic device, according to an embodiment of the present invention.
Figure 11:
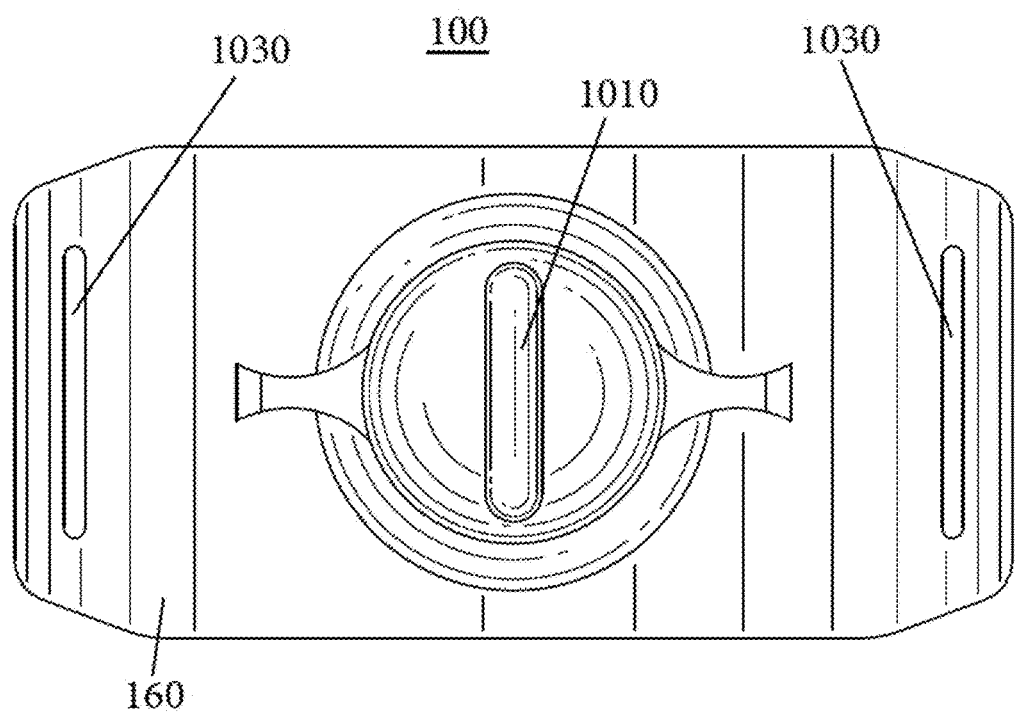
FIG. 11 shows a top view of a vibrating haptic device, according to an embodiment of the present invention.
Figure 12:
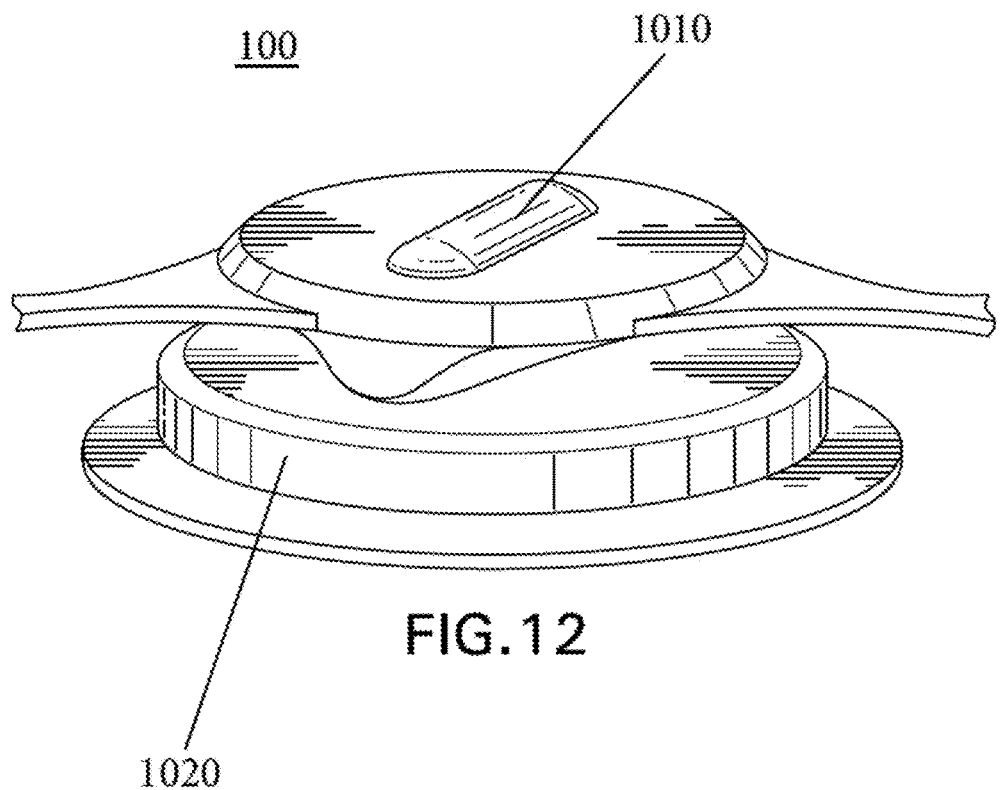
FIG. 12 shows a perspective view of a vibrating haptic device, according to an embodiment of the present invention.
Figure 13:
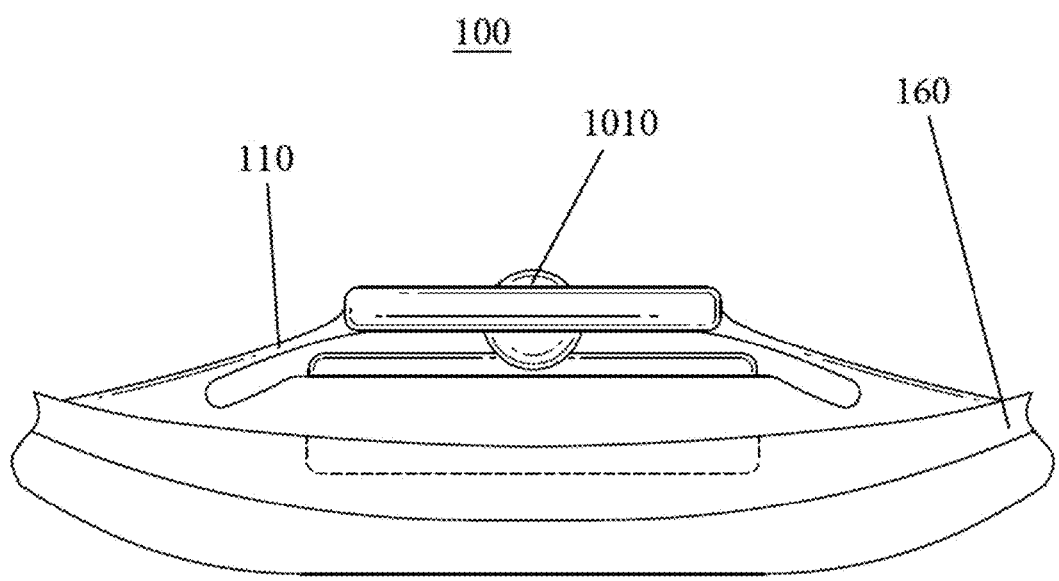
FIG. 13 shows a close-up side view of a vibrating haptic device, according to an embodiment of the present invention.

Key components inside the vibrating haptic device 100 (also shown in FIG. 9) are the custom PCB 130, isolation pad 140, and multiple haptic actuators 150. These actuators 150 can be of any shape or form. According to an exemplary embodiment, two piezoelectric actuators 150 are housed in the band 160. Multiple actuators 150 are necessary to have a high level of tactile output, as double strength, alternate patterns, and directional bias to the haptic signals can be output (i.e., if a left turn is approaching, only the left side of the vibrating haptic device 100 will have a vibration pattern; if a right turn is approaching, only the right side of the vibrating haptic device 100 will have a vibration pattern; if the user is traveling in the wrong direction, the signal that communicates "incorrect" are multiple actuators 150 alternating rapidly at full strength; high definition compass mode; etc).

According to an embodiment, the one or more actuators 150 include a combination of a 3-in-1 Linear resonating mass system. The motors will follow similar to linear resonating actuators (LRAs). According to an embodiment, instead of moving a sing mass up and down using electromagnetic coils, these actuators 150 are configured such that each mass is a concentric ring that can be activated as individual or in varying combination.

According to an embodiment, creating seven distinct frequencies (based on the natural harmonics of the weight combinations) in one single actuator 150 device provide a tactile frequency range of a speaker, while drastically minimizing power consumption due to discreet activation only at exacting frequencies.

Compass mode is the idea that the user, relative to his/her chosen destination, is at some angular degree of correct/incorrect. According to an embodiment, the vibrating haptic device 100 expresses a logarithmic relation between strength of the haptic feedback to the angle, which is an intuitive way to express "wrong way, right way". For example, if the user is facing 0 degrees towards destination(A), there is no haptic feedback, except for very faint, intermittent (confirmation). In contrast, at 180 degrees towards destination(A), there is 100% feedback; "high definition compass mode" mentioned previously would be the same concept, except the weighted actuation signals to users if he/she is (−) degrees to destination(A) or (+) degrees to destination(A).

According to an embodiment, the angle at which there is little to no haptic feedback is more than just 1 degree, so as to give the user some freedom to walk. According to an embodiment, this parameter is adjustable. This parameter is referred to as "the corridor". The corridor may have a width and angle (1220, shown in FIG. 8FIG. 8). According to an embodiment, GPS routing data done on the application is taken and used to create a series of destination(A)s, so that the user isn't just being guided to 1 single destination, but rather along a calculated route. The multiple points 1210 (shown in FIG. 8FIG. 8) on a route are also used towards the custom navigation algorithm, increasing or decreasing distance between points to accommodate, resulting in a smooth navigation experience.

Privacy is important to many users. According to an embodiment, the haptic device 100 incorporates variations of blockchain security protocols to safely disconnect a user's identity from their location data being collected.

Figure 7:
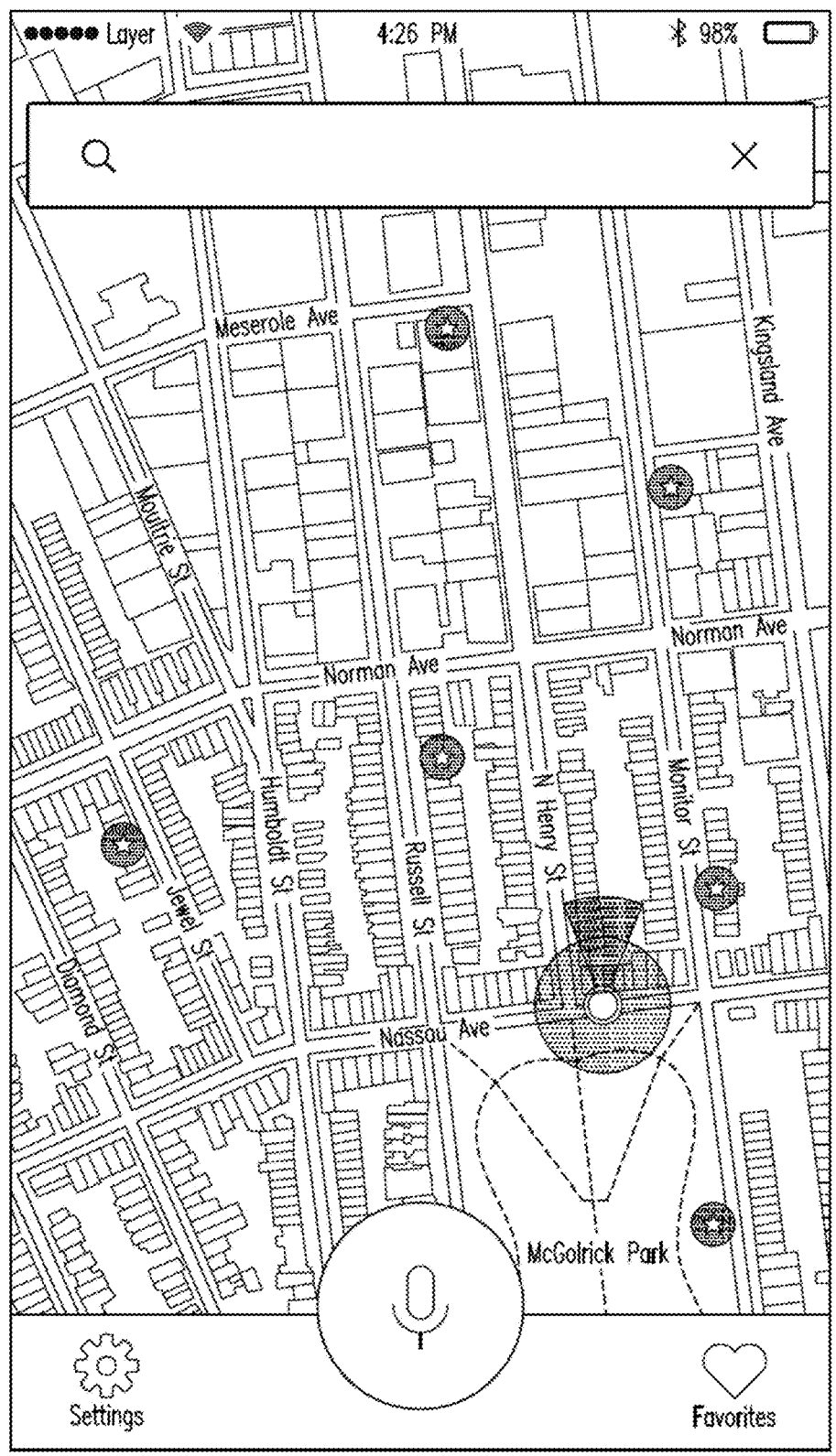

Various screenshots of the application are shown, in FIGS. 2-7, in accordance with various embodiments of the present invention. These screenshots illustrate an introduction screen (FIG. 2), a navigation input screen (FIG. 3), including a display map, a voice input screen (FIG. 4) (wherein a user can use voice recognition hardware and software to input a destination), a start screen to begin the navigation (FIG. 5), an arrival screen (FIG. 6), and one or more display maps (FIG. 7). According to an embodiment, the display maps may include one or more Points of Interest (POIs).

It is noted that other visual displays may also be used in conjunction with the application. It is also noted that the user may input the final destination using text, voice recognition, and/or any other suitable form of input means. It is further noted that any screen of the present application may be configured to enable a user to input one or more destinations by any suitable means.

According to an embodiment, the application is configured to provide users with haptic feedback, as a means of communicating where to go/what to do, etc. (e.g., if a user glides a finger over a maps section POIs will "tap" whenever the user's fingertip crosses over them—almost like braille on the phone 1200. The user would then, e.g., long press on these POIs, and more information would appear, or said POI would become the next navigation point.

According to an embodiment, the haptic device 100 is configured to enable users to navigate indoors and/or outdoors. According to an embodiment, the application and haptic device 100 are configured to have a smooth transition between indoor and outdoor navigation. According to an embodiment, the haptic device 100 and/or the application further presents the user with the user's elevation. According to an embodiment, for indoor use, the device 100 and/or application may, for spaces mapped for public use (e.g., airports, museums, train stations, etc . . . ) be configured to leverage existing beacon technology or HD interior scans to give users their exact position in space and deliver them to their destination using haptics.

According to an embodiment, the haptic feedback device 100 may not only enable users to customize how the users navigate individually, but also how the users will navigate as a member of a community. According to an embodiment, groups of users may be enabled to get together to explore new areas, either suggested by other aggregate members or suggested by data and/or paying advertisers (e.g., being rerouted from a route because of construction and querying where is the safest / fastest route to take?).

Referring now to FIGS. 10-13, a side view (FIG. 10) (and close-up side view (FIG. 13)), a top view (FIG. 11), and a perspective view of a vibrating haptic device 100 are illustratively depicted, in accordance with an embodiment of the present invention.

According to the embodiment shown in FIGS. 1-13, a dampening gel 1030 is positioned below the motor 1010 and the haptic actuator 150. According to an embodiment, the dampening gel 1020 dampens the force produced by the haptic actuator 150. According to an embodiment, the dampening gel 1020 is highly malleable and includes a soft nylon gel. According to an embodiment, the dampening gel 1030 includes soft, malleable silicon. It is noted, however, that any suitable dampening gel 1020 material may be used, while maintaining the spirit of the present invention.

According to an embodiment, one or more of the top enclosure 110 and/or bottom enclosure 160 may include rubber, silicon, and/or any other suitable material. According to an embodiment, the bottom enclosure 160 may include one or more openings 1030 for the connection of a strap 170 and/or any other suitable securing device.

Figure 14:
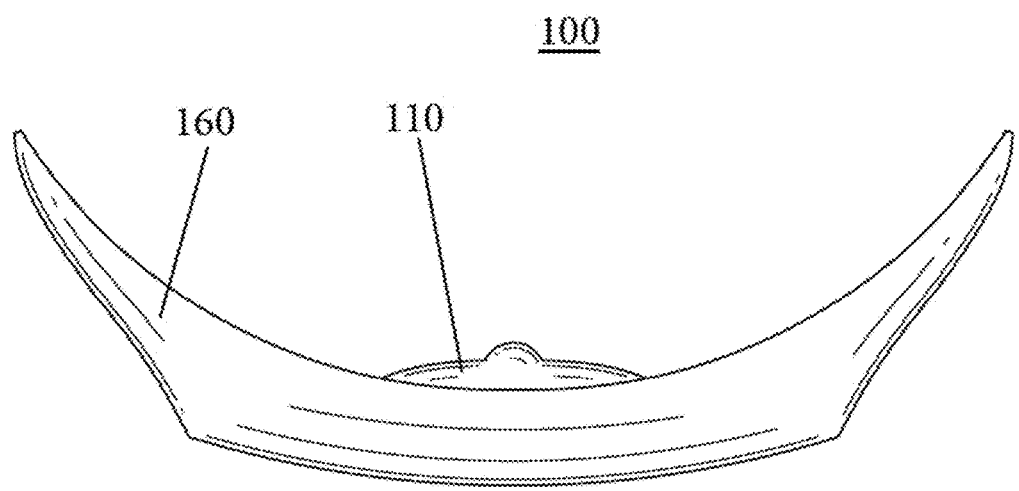
FIG. 14 shows a side view of a vibrating haptic device, according to an embodiment of the present invention.
Figure 15:
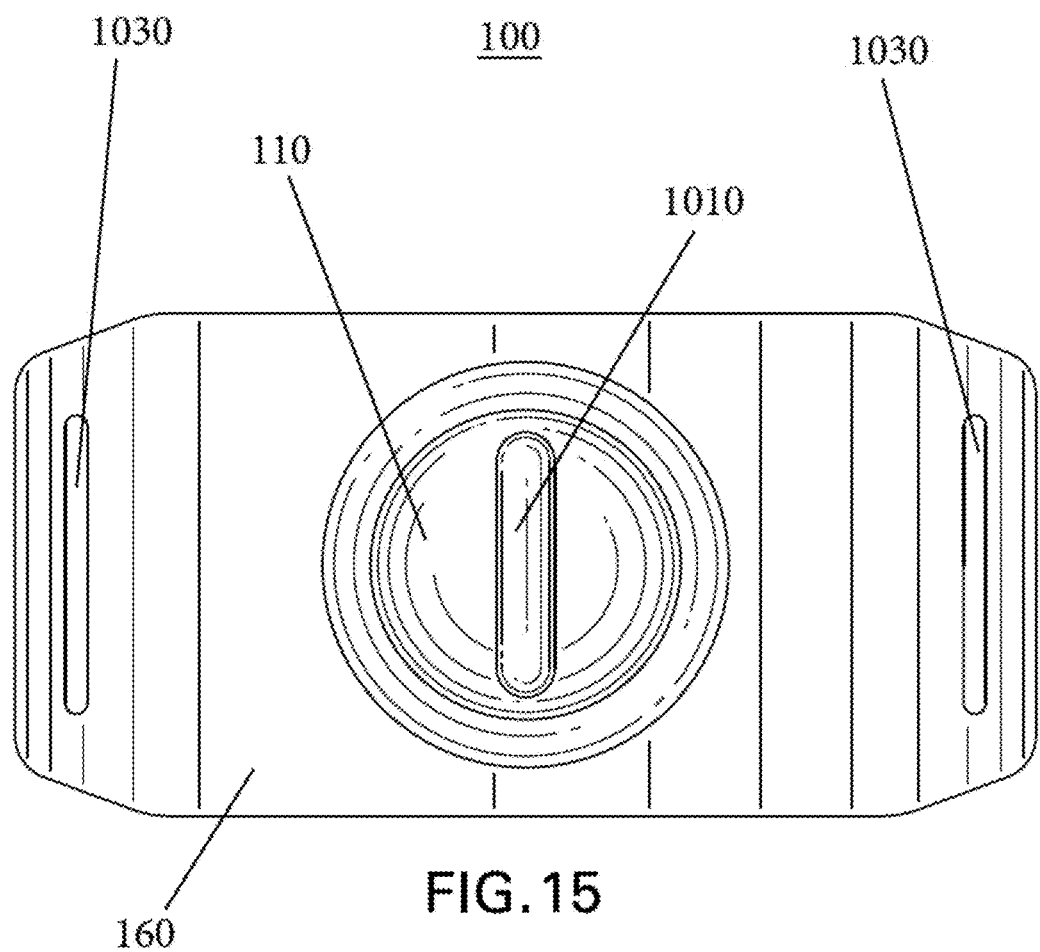
FIG. 15 shows a top view of a vibrating haptic device, according to an embodiment of the present invention.

Referring now to FIGS. 14-15, a side view (FIG. 14) and a top view (FIG. 15) of a vibrating haptic device 100 are illustratively depicted, in accordance with an embodiment of the present invention.

According to the embodiment shown in FIGS. 14-15, the top enclosure 110 is fully enclosed over the bottom enclosure 160. According to an embodiment, the top enclosure 110 is formed from a highly malleable silicon mold. It is noted, however, that any suitable material may be used, while maintaining the spirit of the present invention.

Figure 16:
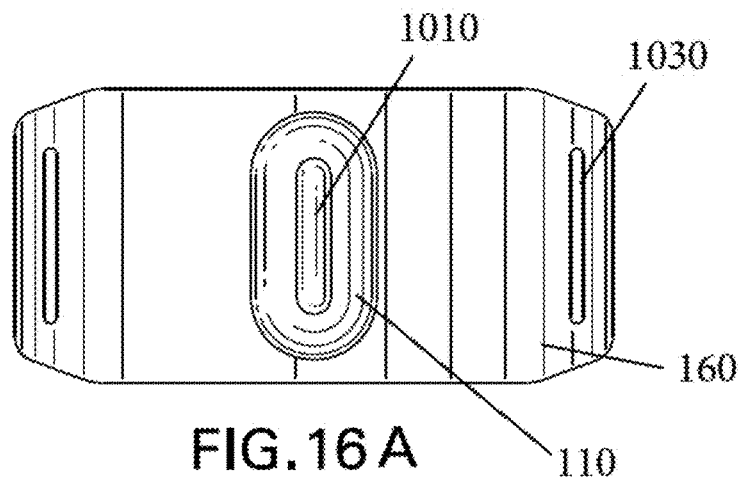
FIG. 16A shows a top view of a vibrating haptic device, according to an embodiment of the present invention.
FIG. 16B shows a cutout side view of the top enclosure of the vibrating haptic device of FIG. 16A, according to an embodiment of the present invention.
FIG. 16C shows a top view of a vibrating haptic device, according to an embodiment of the present invention.
FIG. 16D shows a cutout side view of the top enclosure of the vibrating haptic device of FIG. 16C, according to an embodiment of the present invention.
Figure 16:
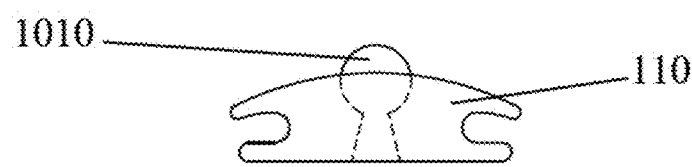
Figure 16:
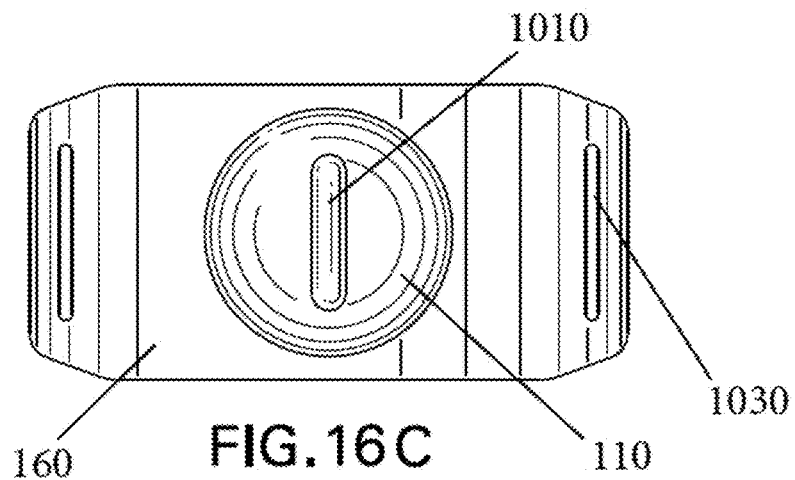
Figure 16:
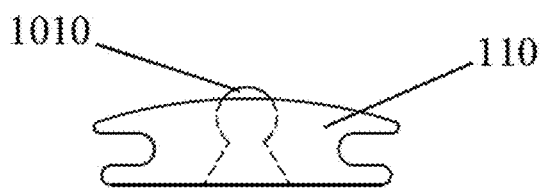
Figure 17:
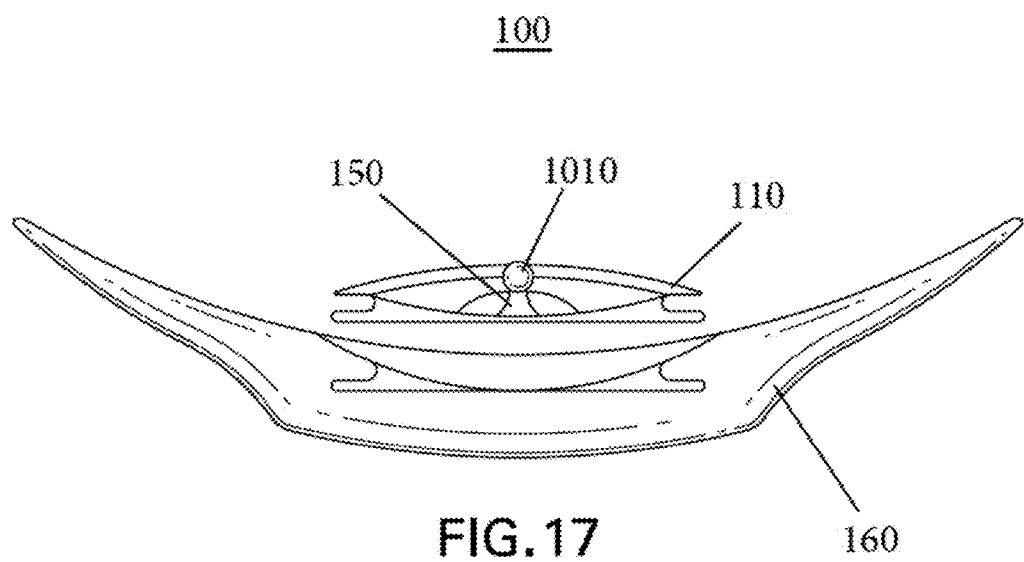
FIG. 17 shows a partially exploded view of a vibrating haptic device, according to an embodiment of the present invention.

It is noted that the top enclosure 110 may take the form of various geometric shapes (as shown in FIGS. 16A-C). It is also noted that the bottom enclosure 160 may include an opening configured to receive the top enclosure 110 (as shown in FIG. 17).

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A wearable device for aiding in navigation, comprising:
a vibrating haptic device configured to connect to a unique algorithm for non-visual and non-audial navigation, wherein the unique algorithm makes the vibrating haptic device change haptic patterns based on an activity of a user wearing the wearable device such that the user is directed to follow directions for arriving to a point of interest, the vibrating haptic device further including:
a printed circuit board,
wherein the printed circuit board includes a geolocation tracking system and is configured to determine coordinates of the user;
a battery;
one or more isolation pads;
a plurality of actuators comprising a combination of a 3-in-1 linear resonating mass system so that each actuator of the plurality of actuators is configured to create seven distinct frequencies to provide a tactile frequency range of a speaker while minimizing power consumption; and
an enclosure configured to house the printed circuit board, the battery, the one or more isolation pads, and the plurality of actuators,
wherein the enclosure is further configured to be secured to a wrist of the user.

2. The wearable device as recited in claim 1, wherein the printed circuit board is a flexible printed circuit board.

3. The wearable device as recited in claim 1, further comprising a strap for coupling the device to the user.

4. The wearable device as recited in claim 1, wherein the battery is a rechargeable battery.

5. The wearable device as recited in claim 1, wherein the isolation pads are configured to mechanically separate the actuators.

6. The wearable device as recited in claim 1, wherein the geolocation tracking system is a radionavigation system.

7. The wearable device as recited in claim 6, wherein the radionavigation system includes a Global Positioning System (GPS) transceiver.

8. A system for aiding in navigation, comprising:
a vibrating haptic device configured to connect to a unique algorithm for non-visual and non-audial navigation, wherein the unique algorithm makes the vibrating haptic device change haptic patterns based on an activity of a user wearing the wearable device such that the user is directed to follow directions for arriving to a point of interest, the vibrating haptic device further, including:
a printed circuit board,
wherein the printed circuit board includes a geolocation tracking system and is configured to gather data pertaining to coordinates of the user;
a battery;
one or more isolation pads; and
a plurality of actuators comprising a combination of a 3-in-1 linear resonating mass system so that each actuator of the plurality of actuators is configured to create seven distinct frequencies to provide a tactile frequency range of a speaker while minimizing power consumption; and
a mobile electronic device coupled to the vibrating haptic device, wherein the mobile electronic device is configured to analyze data gathered by the vibrating haptic device and determine the geographic position of the user and an angle of the user.

9. The system as recited in claim 8, further comprising an enclosure configured to house the printed circuit board, the battery, the one or more isolation pads, and the plurality of actuators.

10. The system as recited in claim 8, wherein the printed circuit board is a flexible printed circuit board.

11. The system as recited in claim 8, further comprising a strap for coupling the vibrating haptic device to the user.

12. The system as recited in claim 8, wherein the battery is a rechargeable battery.

13. The system as recited in claim 8, wherein the isolation pads are configured to mechanically separate the actuators.

14. The system as recited in claim 8, wherein the plurality of actuators are selected from the group consisting of:
    piezoelectric actuators;
    eccentric rotating mass actuators;
    linear resonant actuators; and
    bone conduction speakers.

15. The system as recited in claim 8, wherein the geolocation tracking system is a radionavigation system.

16. The system as recited in claim 15, wherein the radionavigation system includes a Global Positioning System (GPS) transceiver.

* * * * *